US011857659B2

(12) United States Patent
Verhovnik et al.

(10) Patent No.: US 11,857,659 B2
(45) Date of Patent: Jan. 2, 2024

(54) RINSE-OFF CONDITIONER COMPOSITIONS COMPRISING MICROCAPSULES

(71) Applicant: FIRMENICH SA, Satigny (CH)

(72) Inventors: Glenn Verhovnik, Geneva (CH); Arnaud Struillou, Geneva (CH); Daniel Reichlin, Geneva (CH)

(73) Assignee: FIRMENICH SA, Geneva (CH)

( * ) Notice: Subject to any disclaimer, the term of this patent is extended or adjusted under 35 U.S.C. 154(b) by 531 days.

(21) Appl. No.: 16/616,904

(22) PCT Filed: Jun. 14, 2018

(86) PCT No.: PCT/EP2018/065761
§ 371 (c)(1),
(2) Date: Nov. 25, 2019

(87) PCT Pub. No.: WO2018/229175
PCT Pub. Date: Dec. 20, 2018

(65) Prior Publication Data
US 2021/0145719 A1 May 20, 2021

(30) Foreign Application Priority Data
Jun. 15, 2017 (EP) .................................. 17176256

(51) Int. Cl.
*A61K 8/11* (2006.01)
*A61Q 5/02* (2006.01)
*A61Q 5/12* (2006.01)
*A61Q 19/00* (2006.01)
*A61K 8/41* (2006.01)
*A61K 8/31* (2006.01)
*A61K 8/34* (2006.01)
*A61K 8/36* (2006.01)
*A61K 8/73* (2006.01)
*A61K 8/88* (2006.01)
*A61K 8/898* (2006.01)
*A61K 8/92* (2006.01)

(52) U.S. Cl.
CPC ............... *A61K 8/416* (2013.01); *A61K 8/11* (2013.01); *A61K 8/31* (2013.01); *A61K 8/342* (2013.01); *A61K 8/361* (2013.01); *A61K 8/737* (2013.01); *A61K 8/88* (2013.01); *A61K 8/898* (2013.01); *A61K 8/922* (2013.01); *A61K 8/927* (2013.01); *A61Q 5/02* (2013.01); *A61Q 5/12* (2013.01); *A61Q 19/007* (2013.01); *A61K 2800/33* (2013.01); *A61K 2800/412* (2013.01); *A61K 2800/5426* (2013.01); *A61K 2800/624* (2013.01)

(58) Field of Classification Search
CPC ............... A61K 8/11; A61K 2800/412; A61K 2800/654
See application file for complete search history.

(56) References Cited

U.S. PATENT DOCUMENTS

| 4,234,627 A | 11/1980 | Schilling |
| 4,973,422 A | 11/1990 | Schmidt |
| 5,185,155 A | 2/1993 | Behan et al. |
| 2003/0017246 A1 | 1/2003 | Alamian et al. |
| 2004/0071742 A1 | 4/2004 | Popplewell et al. |
| 2006/0210509 A1 | 9/2006 | Johnson et al. |
| 2007/0110695 A1* | 5/2007 | Hoffmann ............... A61Q 5/12 424/70.28 |
| 2009/0071493 A1* | 3/2009 | Nguyen ............... A61K 8/736 132/202 |
| 2012/0103357 A1* | 5/2012 | Hoffmann ............ A61K 8/585 132/202 |
| 2014/0322283 A1* | 10/2014 | Berthier ............... C11D 3/505 514/556 |
| 2016/0256364 A1* | 9/2016 | Dihora ................. A61Q 5/12 |

FOREIGN PATENT DOCUMENTS

| EP | 2300146 B1 | 3/2017 |
| EP | 2579976 B1 | 8/2017 |
| WO | 03002699 A1 | 1/2003 |
| WO | 2007004166 A1 | 1/2007 |
| WO | 2012138690 A2 | 10/2012 |
| WO | 2013068255 A1 | 5/2013 |
| WO | 2013092375 A1 | 6/2013 |
| WO | 2015110568 A1 | 7/2015 |
| WO | 2015189309 A1 | 12/2015 |
| WO | 2016193435 A1 | 12/2016 |
| WO | 2017001385 A1 | 1/2017 |

OTHER PUBLICATIONS

International Search Report and Written Opinion for International Application No. PCT/EP2018/065761, dated Jul. 27, 2018, 13 pages.

* cited by examiner

Primary Examiner — Robert T. Crow
Assistant Examiner — John P Nguyen
(74) Attorney, Agent, or Firm — Armstrong Teasdale LLP

(57) ABSTRACT

Described herein are rinse-off hair conditioner compositions with high deposition properties for cationically coated microcapsules. The compositions contain limited amounts of quaternary ammonium salts that are replaced by at least one non-quaternized conditioning ingredient to provide a high deposition of microcapsules onto a surface.

16 Claims, No Drawings

RINSE-OFF CONDITIONER COMPOSITIONS COMPRISING MICROCAPSULES

CROSS-REFERENCE TO RELATED APPLICATIONS

This application is a U.S. National Phase Application of PCT/EP2018/065761, filed on Jun. 14, 2018, which claims the benefit of priority to European Patent Application Number 17176256.0, filed Jun. 15, 2017, the entire contents of which are hereby incorporated by reference herein.

TECHNICAL FIELD

The present invention relates to rinse-off conditioner compositions comprising microcapsules having an oil-based core and a polymeric shell coated with at least a cationic polymer. The compositions of the invention are characterized by the fact that they comprise a limited amount of quaternary ammonium salts that is counterbalanced by an optimized amount of non-quaternized conditioning ingredients, which maximize the deposition of microcapsules on a surface such as hair or skin.

BACKGROUND OF THE INVENTION

Microencapsulation is an efficient technology to stabilize volatile materials and to efficiently deliver such active benefit materials e.g. perfume oils, onto various surfaces such as hair, skin or fabrics. Microcapsules, in particular those that contain an oil-based core and a polymeric shell so called core-shell microcapsules, are therefore nowadays widely used in many consumer products.

When used as part of rinse-off formulations, it is desired to maximise the amount of capsules remaining on the targeted surface after the rinsing process. The addition of cationic deposition aids either to the capsule shell or directly into the rinse-off product has been described in various patents as a way to improve capsules deposition efficiency. One may cite for instance U.S. Pat. Nos. 4,234,627, 4,973,422, 5,185,155, US 20040071742, WO 03/002699 and US 2003/017246 as examples of such disclosures.

In WO 2017/001385, the Applicant has previously described the enhanced deposition of microcapsules having a cationic coating made of a mixture of cationic polymers.

Among consumer products for which a high deposition is desired, one may cite rinse-off conditioners. Typical ingredients of those compositions are non-quaternized conditioning ingredients used most of the time in combination with quaternary ammonium salts and water soluble cationic conditioning polymers to provide good conditioning performance.

The performance in terms of capsule deposition from existing rinse-off conditioning formulations could be improved.

There is therefore a need to provide rinse-off conditioner compositions that would exhibit high performance in terms of microcapsule deposition.

The present invention solves the above problem with a rinse-off conditioner composition comprising microcapsules having an oil-based core and a polymeric shell coated with at least a cationic polymer, said composition comprising a low amount of quaternary ammonium salts and an optimized amount of non-quaternized conditioning ingredients.

SUMMARY OF THE INVENTION

A first object of the invention is a rinse-off conditioner composition comprising:

a core-shell microcapsules slurry comprising microcapsules having an oil-based core and a polymeric shell coated with at least one cationic polymer;
up to 4 wt % by weight of at least one quaternary ammonium salt;
from 0.25 to 15 wt % by weight of at least one non quaternized conditioning ingredient comprising an oil or a wax or a mixture thereof;
less than 2% by weight of at least one water soluble cationic conditioning polymer; based on the total weight of the composition.

A second object of the invention is the use of a composition as defined above for depositing microcapsules on a surface, preferably on hair and/or skin.

DETAILED DESCRIPTION OF THE INVENTION

Unless stated otherwise, percentages (%) are meant to designate percent by weight of a composition.

The present invention now has determined a way to improve the efficiency in depositing microcapsules on a substrate in rinse-off conditioning applications. What is referred to as improving deposition or improving deposition efficiency is the percentage of microcapsules that remains on a substrate during use, in particular that remains on a substrate after a rinsing step. Better deposition translates then into an improvement in the delivery performance of the active ingredient encapsulated, for instance the olfactive performance in the case of a perfume, meaning that the microcapsules are able to deliver long lasting perception of a fragrance. It has been surprisingly found that the full or partial replacement of quaternary ammonium salts by non quaternized conditioning ingredients and optionally by water soluble cationic conditioning polymers in a composition comprising cationically coated microcapsules could significantly improve the performance of those microcapsules in terms of deposition.

A first object of the invention is therefore a rinse-off conditioner composition comprising:

a core-shell microcapsules slurry comprising microcapsules having an oil-based core and a polymeric shell coated with at least one cationic polymer;
up to 4 wt % by weight of at least one quaternary ammonium salt;
from 0.25 to 15 wt % by weight of at least one non quaternized conditioning ingredient comprising an oil or a wax or a mixture thereof;
less than 2% by weight of at least one water soluble cationic conditioning polymer;
based on the total weight of the composition.

Core-Shell Microcapsules

A "core-shell microcapsule", or the similar, in the present invention is meant to designate a capsule that has a particle size distribution in the micron range (e.g. a mean diameter (d(v, 0.5)) comprised between about 1 and 3000 μm) and comprises an external solid oligomer-based shell or a polymeric shell and an internal continuous phase enclosed by the external shell.

The core-shell microcapsule according to the invention comprises an oil-based core. By "oil", it is meant an organic phase that is liquid at about 20° C. which forms the core of the core-shell capsules. According to any one of the invention embodiments, said oil comprises an ingredient or composition selected amongst a perfume, perfume ingredient, flavour, flavour ingredient, nutraceuticals, cosmetic ingredient, sunscreen agent, insecticide, malodour counteracting substance, bactericide, fungicide, biocide actives, insect repellent or attractant, insect control agent, drug, agrochemical ingredient and mixtures thereof.

According to a particular embodiment, said oil-based core comprises a perfume with another ingredient selected from the group consisting of nutraceuticals, cosmetics, insect control agents and biocide actives.

According to a particular embodiment, the oil-based core comprises a perfume or flavour. According to a preferred embodiment, the oil-based core comprises a perfume. According to another embodiment, the oil-based core consists of a perfume.

By "perfume oil" (or also "perfume") what is meant here is an ingredient or composition that is a liquid at about 20° C. According to any one of the above embodiments said perfume oil can be a perfuming ingredient alone or a mixture of ingredients in the form of a perfuming composition. As a "perfuming ingredient" it is meant here a compound, which is used for the primary purpose of conferring or modulating an odour. In other words such an ingredient, to be considered as being a perfuming one, must be recognized by a person skilled in the art as being able to at least impart or modify in a positive or pleasant way the odor of a composition, and not just as having an odor. For the purpose of the present invention, perfume oil also includes combination of perfuming ingredients with substances which together improve, enhance or modify the delivery of the perfuming ingredients, such as perfume precursors, emulsions or dispersions, as well as combinations which impart an additional benefit beyond that of modifying or imparting an odor, such as long-lasting, blooming, malodour counteraction, antimicrobial effect, microbial stability, insect control.

The nature and type of the perfuming ingredients present in the oil phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredients may be dissolved in a solvent of current use in the perfume industry. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn® or benzyl benzoate. According to a particular embodiment, the solvent comprises low odour, high density materials like benzyl salicylate, cyclohexyl salicylate, hexyl salicylate. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

The nature of the polymeric shell of the microcapsules of the invention can vary. As non-limiting examples, the shell can be made of a polymeric material selected from the group consisting of polyurea, polyurethane, polyamide, polyacrylate, polysiloxane, polycarbonate, polysulfonamide, urea formaldehyde, melamine formaldehyde resin, melamine urea resin, melamine glyoxal resin, gelatin/gum arabic shell wall, and mixtures thereof.

The shell can also be hybrid, namely organic-inorganic such as a hybrid shell composed of at least two types of inorganic particles that are cross-linked, or yet a shell resulting from the hydrolysis and condensation reaction of a polyalkoxysilane macro-monomeric composition.

According to an embodiment, the shell comprises an aminoplast copolymer, such as melamine-formaldehyde or urea-formaldehyde or cross-linked melamine formaldehyde or melamine glyoxal.

According to a particular embodiment, the core-shell microcapsules are cross-linked melamine formaldehyde microcapsules obtainable by a process comprising the steps of:

1) admixing a perfume oil with at least a polyisocyanate having at least two isocyanate functional groups to form an oil phase;
2) dispersing or dissolving into water an aminoplast resin and optionally a stabilizer to form a water phase;
3) adding the oil phase to the water phase to form an oil-in-water dispersion, wherein the mean droplet size is comprised between 1 and 100 microns, by admixing the oil phase and the water phase;
4) performing a curing step to form the wall of said microcapsule; and
5) optionally drying the final dispersion to obtain a dried core-shell microcapsule.

This process is described in more details in WO 2013/092375 & WO 2015/110568, the contents of which are included by reference.

According to another embodiment the shell is polyurea-based made from, for example but not limited to isocyanate-based monomers and amine-containing crosslinkers such as guanidine carbonate and/or guanazole. Preferred polyurea-based microcapsules comprise a polyurea wall which is the reaction product of the polymerisation between at least one polyisocyanate comprising at least two isocyanate functional groups and at least one reactant selected from the group consisting of an amine (for example a water soluble guanidine salt and guanidine); a colloidal stabilizer or emulsifier; and an encapsulated perfume. However, the use of an amine can be omitted.

According to another embodiment, the shell is polyurethane-based made from, for example but not limited to polyisocyanate and polyols, polyamide, polyester, etc.

According to a particular embodiment the colloidal stabilizer includes an aqueous solution of between 0.1% and 0.4% of polyvinyl alcohol, between 0.6% and 1% of a cationic copolymer of vinylpyrrolidone and of a quaternized vinylimidazol (all percentages being defined by weight relative to the total weight of the colloidal stabilizer). According to another embodiment, the emulsifier is an anionic or amphiphilic biopolymer preferably chosen from the group consisting of polyacrylate (and copolymers especially with acrylamide), gum arabic, soy protein, gelatin, sodium caseinate and mixtures thereof.

According to a particular embodiment, the polyisocyanate is an aromatic polyisocyanate, preferably comprising a phenyl, a toluyl, a xylyl, a naphthyl or a diphenyl moiety. Preferred aromatic polyisocyanates are biurets and polyisocyanurates, more preferably a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N).

According to a particular embodiment, the polyisocyanate is a trimethylol propane-adduct of xylylene diisocyanate (commercially available from Mitsui Chemicals under the tradename Takenate® D-110N).

The preparation of an aqueous dispersion/slurry of core-shell microcapsules is well known from a skilled person in the art. In one aspect, said microcapsule wall material may comprise any suitable resin and especially including melamine, glyoxal, polyurea, polyurethane, polyamide, polyester, etc. Suitable resins include the reaction product of an aldehyde and an amine, suitable aldehydes include, formaldehyde and glyoxal. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof. Suitable materials for making may be obtained from one or more of the following companies Solutia Inc. (St Louis, Mo. U.S.A.), Cytec Industries (West Paterson, N.J. U.S.A.), Sigma-Aldrich (St. Louis, Mo. U.S.A.).

According to a particular embodiment, the core-shell microcapsule is a formaldehyde-free capsule. A typical process for the preparation of aminoplast formaldehyde-free microcapsules slurry comprises the steps of:
1) preparing an oligomeric composition comprising the reaction product of, or obtainable by reacting together
   a) a polyamine component in the form of melamine or of a mixture of melamine and at least one $C_1$-$C_4$ compound comprising two $NH_2$ functional groups;
   b) an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between 1/1 and 10/1; and
   c) a protic acid catalyst;
2) preparing an oil-in-water dispersion, wherein the droplet size is comprised between 1 and 600 um, and comprising:
   i. an oil;
   ii. a water medium
   iii. at least an oligomeric composition as obtained in step 1;
   iv. at least a cross-linker selected amongst
   A) $C_4$-$C_{12}$ aromatic or aliphatic di- or tri-isocyanates and their biurets, triurets, trimmers, trimethylol propane-adduct and mixtures thereof; and/or
   B) a di- or tri-oxiran compounds of formula
      A-(oxiran-2-ylmethyl)$_n$
      wherein n stands for 2 or 3 and 1 represents a $C_2$-$C_6$ group optionally comprising from 2 to 6 nitrogen and/or oxygen atoms;
   v. optionally a $C_1$-$C_4$ compounds comprising two $NH_2$ functional groups;
3) heating said dispersion;
4) cooling said dispersion.

This process is described in more details in WO 2013/068255, the content of which is included by reference.

According to another embodiment, the shell of the microcapsule is polyurea- or polyurethane-based. Examples of processes for the preparation of polyurea and polyurethane-based microcapsule slurry are for instance described in WO2007/004166, EP2300146, EP2579976 the contents of which is also included by reference. Typically a process for the preparation of polyurea or polyurethane-based microcapsule slurry include the following steps:
   a) dissolving at least one polyisocyanate having at least two isocyanate groups in an oil to form an oil phase;
   b) preparing an aqueous solution of an emulsifier or colloidal stabilizer to form a water phase;
   c) adding the oil phase to the water phase to form an oil-in-water dispersion, wherein the mean droplet size is comprised between 1 and 500 μm, preferably between 5 and 50 μm;
   d) applying conditions sufficient to induce interfacial polymerisation and form microcapsules in form of a slurry.

Cationic Coating

Microcapsules present in the particular composition of the invention are coated with at least a cationic polymer.

According to the invention, to form the cationic coating on microcapsules, the cationic polymer is added at some stage during the formation of the capsule slurry. In other words, the cationic coating is already present on microcapsules when they are added to the rinse-off conditioner composition and does not come from soluble cationic conditioning polymers or from the quaternary ammonium salts present in the composition.

The microcapsule according to the invention is preferably anionic before coating with the cationic polymer as the preferred emulsifiers are negatively charged polymers. The coating of such an anionic microcapsule with a cationic polymer is well-known from a skilled person in the art.

Cationic polymers are also well known to a person skilled in the art. Preferred cationic polymers have cationic charge densities of at least 0.5 meq/g, more preferably at least about 1.5 meq/g, but also preferably less than about 7 meq/g, more preferably less than about 6.2 meq/g. The cationic charge density of the cationic polymers may be determined by the Kjeldahl method as described in the US Pharmacopoeia under chemical tests for Nitrogen determination. The preferred cationic polymers are chosen from those that contain units comprising primary, secondary, tertiary and/or quaternary amine groups that can either form part of the main polymer chain or can be borne by a side substituent directly connected thereto. The weight average (Mw) molecular weight of the cationic polymer is preferably between 10,000 and 3.5M Dalton, more preferably between 50,000 and 2M Dalton.

According to a particular embodiment, one will use cationic polymers based on acrylamide, methacrylamide, N-vinylpyrrolidone, quaternized N,N-dimethylaminomethacrylate, diallyldimethylammonium chloride, quaternized vinylimidazole (3-methyl-1-vinyl-1H-imidazol-3-ium chloride), vinylpyrrolidone, acrylamidopropyltrimonium chloride, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride. Preferably copolymers shall be selected from the group consisting of polyquaternium-5, polyquaternium-6, polyquaternium-7, polyquaternium 10, polyquaternium-11, polyquaternium-16, polyquaternium-22, polyquaternium-28, polyquaternium-43, polyquaternium-44, polyquaternium-46, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride.

As specific examples of commercially available products, one may cite Salcare® SC60 (cationic copolymer of acrylamidopropyltrimonium chloride and acrylamide, origin: BASF) or Luviquat®, such as the PQ 11N, FC 550 or Style (polyquaternium-11 to 68 or quaternized copolymers of vinylpyrrolidone origin: BASF), or also the Jaguar® (C13S or C17, origin Rhodia).

In the present invention "poly(acrylamidopropyltrimonium chloride-co-acrylamide" and "acrylamidopropyltrimonium chloride/acrylamide copolymer" are used indifferently.

According to any one of the above embodiments of the invention, there is added an amount of cationic polymer comprised between about 0.25 and 2.0 wt %, or even between about 0.5 and 1.5 wt %, percentage being expressed on a w/w basis relative to the total weight of the microcapsule slurry.

According to a particular embodiment, microcapsules are coated with a mixture of at least two cationic polymers. Such microcapsules are disclosed in WO 2017/001385 the content of which is also included by reference.

Quaternary Ammonium Salts

Quaternary ammonium conditioning agents that can be used in the present invention are well known to those skilled in the art. Examples of such compounds are described in US2006/0210509 ([19] to [32]).

It has been found that a composition comprising a reduced amount of quaternary ammonium salts can be used to obtain a high deposition of microcapsules.

Thus, according to the invention, the composition comprises up to 4%, preferably up to 3%, more preferably up to 1.5% by weight of quaternary ammonium salts.

According to an embodiment, the composition comprises between 0 and 4 wt %, more preferably between 0 and 3 wt %, even more preferably between 0 and 1.5 wt % by weight of quaternary ammonium salts based on the total weigh of the composition.

According to another embodiment, the composition comprises between 0.01 and 4 wt %, more preferably between 0.01 and 3 wt %, even more preferably between 0.01 and 1.5 wt %, by weight of quaternary ammonium salts based on the total weigh of the composition.

According to a particular embodiment, the composition is free of quaternary ammonium salts.

Quaternary ammonium salts of the present invention are preferably quaternary ammonium salts bearing at least one long alkyl chain having between 10 carbons and 24 carbons. As non-limiting examples, one may cite behentrimonium chloride, cetrimonium chloride, behentrimonium methosulfate, ester-containing quaternary ammonium salts such as monoesterquats, diesterquats and triesterquats and mixtures thereof.

Surprisingly, it has been found that the partial or total substitution of quaternary ammonium salts with non-quaternized conditioning oils and optionally with water soluble cationic conditioning polymers and copolymers could improve the deposition of microcapsules.

Non-Quaternized Conditioning Ingredients

According to the invention, the non-quaternized conditioning ingredient is preferably hydrophobic or amphiphilic and comprises an oil or a wax or a mixture thereof.

According to an embodiment, the non-quaternized conditioning ingredient is chosen in the group consisting of an oil, a wax and mixture thereof.

According to the invention, the composition comprises between 0.25 and 15% by weight, preferably between 1 and 15%, more preferably between 3 and 15%, even more preferably between 5 and 15%, even more preferably between 6 and 15% by weight of non-quarternized conditioning ingredients based on the total weigh of the composition.

Non quaternized conditioning ingredients can be chosen from the group consisting of polysiloxanes, aminosiloxanes, dimethicone copolyols, alkyl silicone copolymers mineral oil, organic oils such as Macadamia oil, Jojoba oil, sunflower oil, almond oil, olive oil, fatty alcohols such as lanolin alcohol and cetearyl alcohol, fatty acids such as stearic acid, lauric acid, and palmitic acid, fatty acid esters, fatty acid amides such as Bis-Ethyl(Isostearylimidazoline) Isostereamide (Keradyn™ HH), bee wax, and mixtures thereof.

According to a particular embodiment, the non quaternized conditioning ingredient is chosen in the group consisting of stearate esters, cetearyl alcohol, jojoba oil, paraffin oil, bee wax, macadamia oil, lauric acid, olive oil, Bis-Ethyl (Isostearylimidazoline) Isostereamide, amodimethicone, dimethicone, and mixtures thereof.

According to an embodiment, the at least one non quaternized conditioning ingredient is a mixture between cetearyl alcohol and at least one component chosen in the group consisting of jojoba oil, paraffin oil, bee wax, macadamia oil, lauric acid, olive oil, Bis-Ethyl(Isostearylimidazoline) Isostereamide and mixtures thereof.

According to a particular embodiment, the non quaternized conditioning ingredient comprises Jojoba oil, preferably in combination with cetearyl alcohol.

According to another particular embodiment, the non quaternized conditioning ingredient comprises paraffin oil, preferably in combination with cetearyl alcohol.

According to another particular embodiment, the non quaternized conditioning ingredient comprises Bis-Ethyl (Isostearylimidazoline) Isostereamide (Keradyn™ HH), preferably in combination with cetearyl alcohol.

Water Soluble Cationic Conditioning Polymers

The composition of the invention can comprise water soluble cationic conditioning polymers and co-polymers preferably based on quarternized N,N-dimethylaminomethacrylate, diallyldimethylammonium chloride, quarternized vinylimidazole, vinylpyrrolidone, cassia hydroxypropyltrimonium chloride, guar hydroxypropyltrimonium chloride, polygalactomannan 2-hydroxypropyltrimonium chloride ether, starch hydroxypropyltrimonium chloride, cellulose hydroxypropyltrimoniumchloride, polyquaternium-5, polyquaternium-6, polyquaternium-7, polyquaternium-10, polyquaternium-11, polyquaternium-16, polyquaternium-22, polyquaternium-28, polyquaternium-43, polyquaternium-44, polyquaternium-46 and mixtures thereof and copolymers and terpolmers of the above with acrylic acid, methacrylic acid, acrylamide, methylacrylamide and N-vinylpyrrolidone.

The composition comprises less than 2%, preferably less than 1% of water soluble cationic conditioning polymers and co-polymers, preferably from 0.1 to 1% by weight based on the total weigh of the composition.

According to a particular embodiment, the composition is free of water soluble cationic conditioning polymers.

According to a particular embodiment, the composition comprises:
from 0.1 to 5 wt % of a core-shell microcapsules slurry comprising microcapsules having an oil-based core and a polymeric shell coated with at least one cationic polymer;

up to 3 wt % by weight of at least one quaternary ammonium salt, preferably chosen in the group consisting of behentrimonium chloride, cetrimonium chloride, behentrimonium methosulfate, ester-containing quaternary ammonium salts such as monoesterquats, diesterquats and triesterquats and mixtures thereof;

from 5 to 15%, preferably from 6 to 15 wt % by weight of at least one non quaternized conditioning ingredients, preferably chosen in the group consisting of stearate esters, cetearyl alcohol, jojoba oil, paraffin oil, bee wax, macadamia oil, lauric acid, olive oil, Bis-Ethyl(Isostearylimidazoline) Isostereamide, amodimethicone, dimethicone, and mixtures thereof;

less than 1% by weight of water soluble cationic conditioning polymers, preferably chosen in the group consisting of Acrylamidopropyltrimonium Chloride/Acrylamide Copolymer, Guar Hydroxypropyltrimonium Chloride and mixture thereof;

based on the total weight of the composition.

According to an embodiment, the composition of the invention is free of anionic, amphoteric or zwitterionic surfactants.

Other Ingredients

The rinse-off conditioner composition of the invention may comprise one or more ingredients including those well-known in the art for use in rinse-off conditioner such viscosity modifiers, dyes, thickeners, solubilizers, foam boosters, perfumes.

The composition may be in the form of a liquid, having a viscosity preferably comprised between 1500 and 30 000 cPs, preferably between 4000 and 30,000 cPs, more preferably between 5000 and 25,000 cPs.

Viscosities were measured 24 hours after the sample preparation with a BROOKFIELD viscosimeter DV-II+at 20 rpm with spindle 5 at 25° C.

According to an embodiment, the composition comprises a cosmetically acceptable aqueous phase that may be present at a level of from about 20% to about 95%, preferably from about 60% to about 85%. The cosmetically acceptable aqueous phase may be selected from the group consisting of water and water solutions of lower alkyl alcohols and polyhydric alcohols. The lower alkyl alcohols may be monohydric alcohols having 1 to 6 carbons. In an embodiment, the lower alkyl alcohols are ethanol and isopropanol. The polyhydric alcohols may be ethylene glycol, propylene glycol, hexylene glycol, glycerin, and propane diol. One may also cite Ethylene glycol ethers, polyethylene glycol ethers such as TWEEN-20 or BRIJ S20, polypropylene glycol ethers and polyethylene/polypropylene glycol ethers.

According to an embodiment, the composition of the invention is in the form of a hair conditioner, preferably rinse-off conditioner, conditioning shampoo, skin conditioning rinse-off product such as in-shower lotion.

Another object of the invention is the use of a composition as defined above for depositing microcapsules on a surface, preferably on hair and/or skin.

Another object of the invention is a method for improving deposition of microcapsules on a surface, which comprises treating said surface with the composition of the invention as defined above.

The invention will now be further described by way of examples. It will be appreciated that the invention as claimed is not intended to be limited in any way by these examples.

EXAMPLES

Deposition

For the following examples, the analytical deposition of microcapsules onto hair was measured as described below.

Fragranced microcapsules were added to the rinse-off compositions described in the invention at a dosage of 0.2% encapsulated perfume. The microcapsules contained perfume A described in Example 1, Table 1 and a UV tracer (Uvinul A Plus).

For the quantification of deposition, the following procedure was used. A 500 mg mini brown Caucasian hair swatch was wet with 40 mL of tap water (39° C.). The excess water was gently squeezed out once and 0.1 mL of the conditioner formulation containing microcapsules loaded with a UV tracer were applied. The conditioner was distributed for 30 seconds with gentle rubbing between two fingers. The swatch was then rinsed with 100 mL tap water (39° C.) with 50 mL applied to each side of the swatch. The excess water was gently squeezed out and the hair swatch was then cut into a pre-weighed 20 mL scintillation vial. This process was repeated in triplicate and then the vials containing the cut hair were dried in a vacuum oven at 50-60° C. (100 Torr) for at least 5 hours.

After the drying process, the vials were again weighed to determine the mass of hair in the vials. Controls were also prepared by adding 0.1 mL of the conditioner composition containing microcapsules to an empty vial. 8 mL of absolute ethanol were then added to each vial and they were subjected to 60 min of sonication. After sonication, the samples were filtered through a 0.45 µm PTFE filter and analysed with a HPLC using a UV detector. To determine the percentage of deposition of microcapsules from the conditioner compositions, the amount of Uvinul extracted from the hair samples was compared to the amount of Uvinul extracted from the control samples.

For each deposition measurement, 3 repeat hair swatch samples were prepared and the deposition value is reported as the average value of the three samples. In case, the variation between the depositions measured on each swatch was higher than 5%, another 3 samples were prepared. A high deposition can be considered at measured values of 10% or above, ideally 25% or above.

Viscosity

Viscosities were measured 24 hours after the sample preparation with a BROOKFIELD viscosimeter DV-II+at 20 rpm with spindle 5 at 25° C.

EXAMPLES

Example 1

Preparation of Microcapsules Used in the Invention

In a round bottom flask, melamine (0.91 g), 2,2-dimethoxyethanal (60 wt % in water, 1.37 g), glyoxal (40 wt % in water, 1.73 g) and 2-oxoacetic acid (50 wt % in water, 0.58 g) were dispersed in water (1.48 g) at RT. The pH value of the dispersion was controlled with sodium hydroxide (30 wt % in water, pH=9.5). The reaction mixture was heated at 45° C. for 25 minutes to give a solution. Then water (6.31 g) was added and the resin was stirred at 45° C. for 5 min.

Resin was transferred in a 200 mL beaker. Guanazole (0.60 g) was dissolved in a solution of Ambergum 1221 (2 wt % in water, 27.04 g). The resulting solution was introduced into the beaker. An oil solution of Takenate D-110N (2.15 g) and a perfume oil (composition from TABLE 1) (29.56 g) was added into the aqueous solution. The biphasic reaction mixture was sheared with an Ultra-turrax at 21500 rpm for 2 min. Acetic acid was added to initiate the polycondensation (pH=5.35). The quality of the emulsion was controlled by light microscopy. The emulsion was transferred into a 200 mL Schmizo reactor and was heated at 45° C. for 1 h, then at 60° C. for 1 h and finally at 80° C. for 2 h. A solution of first cationic copolymer namely acrylamidopropyltrimonium chloride/acrylamide copolymer (Salcare SC60, origin BASF) (20 g, 3 wt % in water), and second cationic copolymer polygalactomannan 2-hydroxy propyltrimethylammonium chloride ether (Jaguar C13S, origin Rhodia) (11 g, 1 wt % in water), was then added and the reaction mixture was heated at 80° C. for 30 min. A solution of urea (6.25 g, 50 wt % in water) was finally added to the reaction mixture, which was heated at 80° C. for 30 min.

The zeta potential measured for this capsule was measured to be −37 mV.

TABLE 1

| Composition of perfume A | |
|---|---|
| Raw material | Quantity (g) |
| Carbinol acetate | 2.20 |
| Citronellyl acetate | 16.5 |
| Linalyl acetate | 10.7 |
| Nopyle acetate | 8.0 |
| Terpinyl acetate | 2.10 |
| Verdyl acetate | 2.9 |
| Decanal | 0.1 |
| Hexylcinnamic aldehyde | 13.95 |
| Ethyl 2-methyl-pentanoate | 0.25 |
| Benzyl benzoate | 8.2 |
| Cyclogalbanate | 2.15 |
| Hedione ® [1] | 11.95 |
| Hexyl isobutyrate | 2.60 |
| Nectalactone | 10.35 |
| Oxane | 0.1 |
| Rose oxide [2] | 0.45 |
| Verdyl propionate | 4.35 |
| Beta-ionone | 0.50 |
| Williams ester | 1.25 |
| 2,4-Dimethyl-3-cyclohexene-1-carbaldehyde | 1.40 |

[1] Cyclopentaneacetic acid, 3-oxo-2-pentyl-, methyl ester; origin and trademark from Firmenich SA, Geneva, Switzerland
[2] 4-methyl-2-(2-methyl1-propen-1-yl)tetrahydro-2H-pyran Example 2

Hair Conditioner Rinse-Off Composition According to the Invention

Procedure:

Aqueous solutions of Salcare SC 60 and Tylose H10 Y G4 were prepared and the ingredients in the order listed in Table 2 were mixed together.

TABLE 2

Hair Rinse-off compositions free of alkyl quat and comprising amodimethicone as non-quaternized conditioning ingredient

| Ingredients | 2-A % |
|---|---|
| WATER DEIONIZED | q.s. 100% |
| Acrylamidopropyltrimonium Chloride/Acrylamide Copolymer *[1] 1% aqueous solution | 40 |
| Hydroxyethylcellulose [2] 2% aqueous solution | 20 |
| 28% Amodimethicone** (&) Trideceth-6[3] | 1 |
| Methylchloroisothiazolinone (&)Methylisothiazolinone [4] | 0.1 |
| Cationically coated microcapsules, described in Example 1 | 1 |
| Total actives of cationic water-soluble polymers* | 0.4% |
| Total actives of non-quaternized conditioning oils** | 0.28% |
| Analytical deposition of microcapsules | 18.1% |

[1] SALCARE SC 60, Ciba
[2] TYLOSE H10 Y G4, Shin Etsu
[3] MIRASIL ADM-E, Bluestar Silicone
[4] KATHON CG, Rohm and Haas Composition 2A shows good performance in terms of deposition.

Example 3

Preparation of Hair Conditioner Rinse-Off Composition with Behentrimonium Chloride as Quaternary Ammonium Salt and Cetearyl Alcohol as Non-Quaternized Conditioning Ingredient Procedure:

1/Phase A: mix all ingredients till homogeneous and heat to 70-75° C.

2/Phase B: combine and melt all ingredients of phase B at 70-75° C.

3/At 70-75° C. slowly add Phase B into Phase A while mixing

4/Keep mixing until cooled down to 40° C. and add Phase C while agitating

TABLE 3

Hair Rinse-off compositions with Behentrimonium chloride as quaternary ammonium salt and Cetearyl Alcohol as non-quaternized conditioning ingredient

| | Ingredients | 3-A % | 3-B % | 3-C % | Comparative 3-D % | Comparative 3-E % | Comparative 3-F % |
|---|---|---|---|---|---|---|---|
| A | WATER DEIONIZED | 94.3 | 93.4 | 91.9 | 90.9 | 89.9 | 88.9 |
| | Ethoxy (20) Stearyl Alcohol [1] | 1 | 1 | 1 | 1 | 1 | 1 |
| | Behentrimonium Chloride [2]* | 0 | 1.5 | 3 | 5 | 6 | 7 |
| B | CETEARYL ALCOHOL [3]** | 4.6 | 4 | 4 | 3 | 3 | 3 |
| C | Methylchloroisothiazolinone (&) Methylisothiazolinone [4] | 0.1 | 0.1 | 0.1 | 0.1 | 0.1 | 0.1 |

TABLE 3-continued

Hair Rinse-off compositions with Behentrimonium chloride as quaternary ammonium salt and Cetearyl Alcohol as non-quaternized conditioning ingredient

| Ingredients | 3-A % | 3-B % | 3-C % | Comparative 3-D % | Comparative 3-E % | Comparative 3-F % |
|---|---|---|---|---|---|---|
| Total actives of quaternary ammonium salt * | 0.0% | 1.5% | 3.0% | 5.0% | 6.0% | 7.0% |
| Total actives of non-quaternized conditioning ingredients** | 4.6% | 4.0% | 4.0% | 3.0% | 3.0% | 3.0% |
| Analytical deposition measured on hair | 33.6% | 11.2% | 11.3% | 8.9% | 9.5% | 9.2% |
| Viscosity (sp 5/20 rpm) | 1980 cPs | 3599 cPs | 5399 cPs | 2160 cPs | 3600 cPs | 4320 cPs |

[1] BRIJ S20, solubiliser, Croda
[2] GENAMIN KDMP, Clariant
[3] Lanette O, BASF
[4] KATHON CG, Rohm and Haas

TABLE 4 continued: Hair Rinse-off compositions with Behentrimonium chloride as quaternary ammonium salt and Cetearyl Alcohol as non-quaternized conditioning ingredient

| | Ingredients | 3-G % | 3-H % | 3-I % | 3-J % |
|---|---|---|---|---|---|
| A | WATER DEIONIZED | 95.9 | 94.9 | 93.9 | 92.4 |
| | Ethoxy (20) Stearyl Alcohol [1] | 1 | 1 | 1 | 1 |
| | Behentrimonium Chloride [2]* | 0 | 0 | 0 | 1.5 |
| B | CETEARYL ALCOHOL [3]** | 3 | 4 | 5 | 5 |
| C | Methylchloroisothiazolinone (&) Methylisothiazolinone [4] | 0.1 | 0.1 | 0.1 | 0.1 |
| | Total actives of quaternary ammonium salt * | 0.0% | 0.0% | 0.0% | 1.5% |
| | Total actives of non-quaternized conditioning ingredients** | 3.0% | 4.0% | 5.0% | 5.0% |
| | Analytical deposition of microcapsules measured on hair | 17.5% | 19.2% | 17.0% | 11.4% |
| | Viscosity (sp 5/20 rpm) | 1680 cPs | 2400 cPs | 3180 cPs | 5640 cPs |

[1] BRIJ S20, solubiliser, Croda
[2] GENAMIN KDMP, Clariant
[3] Lanette O, BASF
[4] KATHON CG, Rohm and Haas Conclusion Compositions 3A, 3B, 3C, 3G, 3H and 3I show good performance in terms of deposition compared to comparative composition compositions 3D, 3E and 3F (that comprise an amount of quaternary ammonium salt greater than 4%).

Both, the quaternary ammonium salt and the cetearyl alcohol participated in the final viscosity of the composition which is desired to be at 4000-5000 cPs or higher in order to provide a creamy aspect. This can be obtained at a quaternary ammonium salt dosage of 3 wt % and cetearyl alcohol dosage of 4% (3-C).

Viscosity could be significantly increased at a low quaternary ammonium salt level of 1.5 wt % by increasing the amount of cetearyl alcohol (3-B vs. 3-J).

Example 4

Hair Conditioner Rinse-Off Composition with Behentrimonium Methosulfate as Quaternary Ammonium Salt and Blends of Non-Quaternized Conditioning Ingredient Procedure:

1/Phase A: mix all ingredients till homogeneous and heat to 70-75° C.

2/Phase B: combine and melt all ingredients of phase B at 70-75° C.

3/At 70-75° C. slowly add Phase B into Phase A while mixing

4/Keep mixing until cooled down to 40° C. and add Phase C while agitating

TABLE 5

Hair Rinse-off compositions with Behentrimonium methosulfate as quaternary ammonium salt and blends of non-quaternized conditioning ingredients

| | Ingredients | 4-A % | 4-B % | 4-C % | 4-D % |
|---|---|---|---|---|---|
| A | WATER DEIONIZED | 93.3 | 93.4 | 94.4 | 92.9 |
| | Ethoxy (20) Stearyl alcohol [1] | 1 | 1 | 1 | 1 |
| B | 55% Behentrimonium Methosulfate* (&) 40% Cetyl Alcohol** (&) 5% Butylene Glycol-[2] | 0 | 1.5 | 1.5 | 4 |
| | Bis-Ethyl(Isostearylimidazoline) Isostereamide** [3] | 1 | 1 | 0 | 0 |
| | CETEARYL ALCOHOL** [4] | 4.6 | 4 | 4 | 3 |
| C | Methylchloroisothiazolinone (&) Methylisothiazolinone [5] | 0.1 | 0.1 | 0.1 | 0.1 |
| | Total actives of quaternary ammonium salt * | 0.0% | 0.8% | 0.8% | 2.2% |
| | Total actives of non-quaternized conditioning ingredients** | 6.1% | 5.7% | 4.7% | 4.8% |
| | Analytical deposition of microcapsules, measured on hair | 28.3% | 18.9% | 15.4% | 10.4% |
| | Viscosity (sp 5/20 rpm) | 9000 cPs | 5000 cPs | 7000 cPs | 2000 cPs |

[1] BRIJ S20, Croda
[2] INCROQUAT BEHENYL TMS-50-PA- (MH), Croda
[3] KERADYN™HH, Croda
[4] Lanette O, BASF
[5] KATHON CG, Rohm and Haas Compositions 4A-4D show good performance in terms of deposition. One can note that the addition of Bis-Ethyl (Isostearylimidazoline) Isostereamide (Keradyn™ HH) to cetearyl alcohol has a positive effect on deposition.

Example 5

Hair Conditioner Rinse-Off Composition with Behentrimonium Chloride as Quaternary Ammonium Salt and Blends of Other Conditioning Ingredient Procedure:

1/Phase A: mix all ingredients till homogeneous and heat to 70-75° C.

2/Phase B: combine and melt all ingredients of phase B at 70-75° C.

3/At 70-75° C. slowly add Phase B into Phase A while mixing

4/Keep mixing until cooled down to 40° C. and add Phase C while agitating

TABLE 6a

Hair Rinse-off compositions with Behentrimonium chloride as quaternary salt and blends of other conditioning ingredients

| | Ingredients | 5 % | 5-A % | 5-B % | 5-C % | 5-D % |
|---|---|---|---|---|---|---|
| A | WATER DEIONIZED | 93.4 | 90.9 | 89.4 | 90.9 | 89.4 |
| | Ethoxy (20) Stearyl Alcohol [1] | 1 | 1 | 1 | 1 | 1 |
| | Behentrimonium Chloride [2]* | 1.5 | 0 | 1.5 | 0 | 1.5 |
| B | PARAFFINE OIL***[3] | 0 | 5 | 5 | 0 | 0 |
| | JOJOBA OIL***[4] | 0 | 0 | 0 | 5 | 5 |
| | CETEARYL ALCOHOL***[5] | 3 | 3 | 3 | 3 | 3 |
| C | Methylchloroisothiazolinone (and) Methylisothiazolinone [6] | 0.1 | 0.1 | 0.1 | 0.1 | 0.1 |
| | Total actives of quaternary ammonium salt * | 1.5% | 0.0% | 1.5% | 0.0% | 1.5% |
| | Total actives of non-quaternized conditioning ingredients*** | 3.0% | 8.0% | 8.0% | 8.0% | 8.0% |
| | Analytical deposition of microcapsules measured on hair | 10.7% | 20.0% | 34.0% | 18.2% | 31.8% |
| | Viscosity (sp 5/20 rpm) | 3500 cps | 1980 cps | 2160 cps | 2790 cps | 6000 cps |

[1] BRIJ S20, Croda
[2] GENAMIN KDMP, Clariant
[3] Savonol 40, Savita
[4] PNJ Deodorized Clear Jojoba, Purcell Jojoba International
[5] Lanette O, BASF
[6] KATHON CG, Room and Haas TABLE 6b Hair Rinse-off compositions with Behentrimonium chloride as quaternary ammonium salt and blends of other conditioning ingredients

| | Ingredients | 5-E % | 5-F % | 5-G % | 5-H % |
|---|---|---|---|---|---|
| A | WATER DEIONIZED | 90.9 | 89.4 | 90.9 | 89.4 |
| | Ethoxy (20) Stearyl Alcohol [1] | 1 | 1 | 1 | 1 |
| | Behentrimonium Chloride [2]* | 1.5 | 1.5 | 1.5 | 1.5 |
| B | Bees wax***[3] | 5 | 0 | 0 | 0 |
| | Macadamia oil***[4] | 0 | 5 | 0 | 0 |
| | Lauric acid*** | 0 | 0 | 5 | 0 |
| | Olive oil***[5] | 0 | 0 | 0 | 5 |
| | CETEARYL ALCOHOL***[6] | 3 | 3 | 3 | 3 |
| c | Methylchloroisothiazolinone (and) Methylisothiazolinone [7] | 0.1 | 0.1 | 0.1 | 0.1 |
| | Total actives of quaternary ammonium salt * | 1.5% | 1.5% | 1.5% | 1.5% |
| | Total actives of non-quaternized conditioning ingredients*** | 8.0% | 8.0% | 8.0% | 8.0% |
| | Analytical deposition of microcapsules measured on hair | 13.6% | 11.3% | 14.4% | 11.9% |

[1] BRIJ S20, Croda
[2] GENAMIN KDMP, Clariant
[3] Baerlocher
[4] FRUTAROM
[5] FLORIN AG
[6] Lanette O, BASF
[7] KATHON CG, Room and Haas Conclusion Compositions 5A to 5H present good performance in terms of deposition.

A significant improvement of the deposition is observed when jojoba oil or paraffin oil is used as conditioning oils in addition to cetearyl alcohol.

Example 6

Hair Conditioner Rinse-Off Composition with Mixtures of Quaternary Ammonium Salts and Blends of Non-Quaternized Conditioning Ingredients Procedure:

1/Phase A: disperse TYLOSE in the water till homogeneous, then add remaining ingredients while mixing and heat to 70-75° C.

2/Phase B: combine and melt all ingredients of phase B at 70-75° C.

3/At 70-75° C. slowly add Phase B into Phase A while mixing

4/Keep mixing until cooled down to 40° C. and add ingredients of Phase C while agitating

TABLE 7

Hair Rinse-off compositions with mixtures of alkyl quats and blends of non-quaternized conditioning ingredients

| | Ingredients | 6-A % | 6-B % | 6-C % | 6-D % | Comparative 6-E % | Comparative 6-F % |
|---|---|---|---|---|---|---|---|
| A | WATER DEIONIZED | 86.3 | 86.4 | 83.4 | 82.4 | 81.4 | 82.3 |
| | Ethoxy (20) Stearyl alcohol [1] | | | 1.5 | 1.5 | 1 | 1 |
| | Hydroxyethylcellulose [2] | 1.5 | 1.5 | 1.5 | 1.5 | 1.5 | 1.5 |
| | Behentrimonium Chloride*[3] | | 1.5 | 2 | 2 | 2.5 | 2.5 |
| | Cetrimonium Chloride*[4] | 1.5 | | | | | 1.2 |
| B | 55% Behentrimonium Methosulfate* (&) 40% Cetyl Alcohol** (&) 5% Butylene Glycol[5] | | 1 | 1 | 4 | 4 | |
| | Glycerol Stearate (&) PEG-100 Stearate**[6] | 2.6 | 2.5 | 3 | 3 | 2 | 2 |
| | CETYL ALCOHOL**[7] | | 2 | | | | |
| | Cetearyl Alcohol**[8] | 4 | 3 | 4 | 4 | 4 | 4 |
| | STEARIC PALMITIC ACIDS mixture**[9] | | 0.5 | | | | |
| | Polymethylsiloxane **[10] | 2.5 | | | | | |
| C | 50% Dimethicone ** (&) C12-13 Pareth-4 (&) C12-13 Pareth-23 (&) Salicylic Acid actives [11] | 1.5 | | | | | |
| | 35% Amodimethicone** (&) Trideceth-12 (&) 5% Cetrimonium Chloride* [12] | | 2.5 | 3 | 3 | 3 | 3 |
| | 28% Amodimethicone ** (&) Trideceth-6 actives [13] | | | | 1 | | |
| | PROPYLENE GLYCOL | | | | | | 1 |
| | Methylchloroisothiazolinone (&) Methylisothiazolinone [14] | 0.1 | 0.1 | 0.1 | 0.1 | 0.1 | 0.1 |
| | CITRIC ACID 10% aqueous sol. till pH 3-3.5 | | | 0.5 | 0.5 | 0.5 | 0.4 |
| | Total actives of quaternary ammonium salt * | 1.5% | 1.6% | 2.7% | 2.7% | 4.9% | 6.1% |
| | Total actives of non-quaternized conditioning ingredients** | 9.9% | 8.9% | 8.5% | 8.8% | 8.9% | 8.9% |

TABLE 7-continued

Hair Rinse-off compositions with mixtures of alkyl quats and blends of non-quaternized conditioning ingredients

| Ingredients | 6-A % | 6-B % | 6-C % | 6-D % | Comparative 6-E % | Comparative 6-F % |
|---|---|---|---|---|---|---|
| Analytical deposition of microcapsules measured on hair | 28.3% | 34.0% | 27.5% | 34.9% | 6.1% | 0.2% |
| Viscosity (sp 5/20 rpm) | 12200 cPs | 15500 cPs | 22000 cPs | 21000 cPs | 20000 cPs | 15000 cPs |

[1] BRIJ S20, Croda
[2] TYLOSE H10 Y G4, Shin Etsu
[3] GENAMIN KDM, Clariant
[4] GENAMIN CTAC, Clariant
[5] INCROQUAT BEHENYL TMS-50-PA- (MH), Croda
[6] ARLACEL 165, Croda
[7] Lanette 16, BASF
[8] Lanette O, BASF
[9] Berg + Schmidt
[10] DIMETHICONE 200 fluid 60000 cSt, Dow Corning
[11] XIAMETER MEM 169 1, Dow Corning
[12] XIAMETER MEM-949, Dow Corning
[13] MIRASIL ADM E, Bluestar Silicones
[14] KATHON CG, Rohm and Haas Conclusion The deposition of cationically coated microcapsules from Example 1 was strongly related to the amount of alkyl quats present in the composition. Up to 2.7 wt %, the deposition remained high around 30% (6-A; 6-B, 6-C; 6-D). With the increase of selected non-quaternized conditioning ingredients, the deposition could be increased above 30% (6-B; 6-D). At higher quaternary ammonium salt concentration of 4.9 wt %, the deposition dropped significantly (6-E) and even more significantly at quaternary ammonium salt concentration of 6.1 wt % (6-F).

The invention claimed is:

1. A rinse-off conditioner composition comprising:
   i. a core-shell microcapsules slurry comprising microcapsules having an oil-based core and a polymeric shell coated with at least one cationic polymer;
   ii. up to 4 wt % by weight of at least one quaternary ammonium salt;
   iii. from 0.25 to 15 wt % by weight of at least one non quaternized conditioning ingredient comprising an oil or a wax or a mixture thereof, wherein the at least one non quaternized conditioning ingredient comprises a mixture between cetearyl alcohol and at least one component selected from the group consisting of jojoba oil, paraffin oil, bee wax, macadamia oil, almond oil, sunflower oil, lauric acid, Bis-Ethyl(Isostearylimidazoline) Isostearamide, and mixtures thereof; and
   iv. less than 2% by weight of at least one water soluble cationic conditioning polymer; based on the total weight of the composition, wherein the composition is free of anionic, amphoteric or zwitterionic surfactants.

2. The rinse-off conditioner composition according to claim 1, wherein said composition comprises from 0.1 to 5% by weight of microcapsules slurry.

3. The rinse-off conditioner composition according to claim 1, wherein said composition comprises up to 3% by weight of quaternary ammonium salts.

4. The rinse-off conditioner composition according to claim 1, wherein said composition comprises between 1 and 15% by weight of at least one non quaternized conditioning ingredient.

5. The rinse-off conditioner composition according to claim 1, wherein said composition comprises less than 1% by weight of at least one water soluble cationic conditioning polymer.

6. The rinse-off conditioner composition according to claim 1, wherein the polymeric shell of the microcapsules is based on a polymeric material selected from the group consisting of polyurea, polyurethane, polyamide, polyacrylate, polysiloxane, polycarbonate, polysulfonamide, urea formaldehyde, melamine formaldehyde resin, melamine urea resin, melamine glyoxal resin, gelatin/ gum arabic and mixtures thereof.

7. The rinse-off conditioner composition according to claim 1, wherein the at least one quaternary ammonium salt is chosen from the group consisting of behentrimonium chloride, cetrimonium chloride, behentrimonium methosulfate, ester-containing quaternary ammonium salts, and mixtures thereof.

8. The rinse-off conditioner composition according to claim 1, wherein the at least one water-soluble cationic conditioning polymer is chosen from the group consisting of quarternized N,N-dimethylaminomethacrylate, diallyldimethylammonium chloride, quarternized vinylimidazole, vinylpyrrolidone, cassia hydroxypropyltrimonium chloride, guar hydroxypropyltrimonium chloride, polygalactomannan 2-hydroxypropyltrimonium chloride ether, starch hydroxypropyltrimonium chloride, cellulose hy droxypropyltrim onium chl ori de, polyquaternium-5, polyquaternium-6, polyquaternium-7, polyquaternium-10, polyquaternium-11, polyquaternium-16, polyquaternium-22, polyquaternium-28, polyquaternium-43, polyquaternium-44, polyquaternium-46 and mixtures thereof and copolymers and terpolymers of the above with acrylic acid, methacrylic acid, acrylamide, methylacrylamide and N-vinylpyrrolidone, and mixtures thereof.

9. The rinse-off conditioner composition according to claim 1, wherein the oil-based core comprises a perfume.

10. The rinse-off conditioner composition according to claim 1, comprising:
   i. from 0.1 to 5 wt % of a core-shell microcapsules slurry comprising microcapsules having an oil-based core and a polymeric shell coated with at least one cationic polymer;
   ii. up to 3 wt % of at least one quaternary ammonium salt;
   iii. from 5 to 15 wt %, by weight of at least one non quaternized conditioning ingredient; and iv. less than 1% by weight of water soluble cationic conditioning polymers based on the total weight of the composition.

11. The rinse-off conditioner composition according to claim 1 in the form of a rinse-off hair conditioner, rinse-off conditioning shampoo, or rinse-off skin conditioner.

12. The rinse-off conditioner composition according to claim 1, wherein said composition comprises up to 1.5% by weight of quaternary ammonium salts.

13. The rinse-off conditioner composition according to claim 1, wherein said composition comprises between 3 and 15% by weight of at least one non quaternized conditioning ingredient.

14. The rinse-off conditioner composition according to claim 10, wherein the at least one quaternary ammonium salt is selected from the group consisting of behentrimonium chloride, cetrimonium chloride, behentrimonium methosulfate, ester-containing quaternary ammonium salts, and mixtures thereof.

15. The rinse-off conditioner composition according to claim 10, wherein the water soluble cationic conditioning polymer is selected from the group consisting of Acrylamidopropyltrimonium Chloride/Acrylamide Copolymer, Guar Hydroxypropyltrimonium Chloride and mixture thereof.

16. The rinse-off conditioner composition according to claim 1, wherein the at least one non quaternized conditioning ingredient is a mixture between cetearyl alcohol and at least one component chosen from the group consisting of jojoba oil, paraffin oil, bee wax, macadamia oil, lauric acid, Bis-Ethyl(Isostearylimidazoline) Isostearamide, and mixtures thereof.

* * * * *